(12) United States Patent
O'Mahony et al.

(10) Patent No.: US 12,011,502 B2
(45) Date of Patent: *Jun. 18, 2024

(54) COMPOSITIONS AND METHODS OF ADMINISTERING BACLOFEN

(71) Applicant: AMNEAL PHARMACEUTICALS LLC, Bridgewater, NJ (US)

(72) Inventors: Leonard O'Mahony, Westmeath (IE); John Devane, Dublin (IE); Sharon Hamm, Odessa, FL (US); David Penake, Atlanta, GA (US)

(73) Assignee: AMNEAL PHARMACEUTICALS LLC, Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/984,001

(22) Filed: Nov. 9, 2022

(65) Prior Publication Data

US 2023/0201107 A1 Jun. 29, 2023

Related U.S. Application Data

(63) Continuation of application No. 17/525,298, filed on Nov. 12, 2021, now Pat. No. 11,523,984.

(51) Int. Cl.
*A61K 31/197* (2006.01)
*A61K 9/00* (2006.01)

(52) U.S. Cl.
CPC .......... *A61K 9/0019* (2013.01); *A61K 31/197* (2013.01)

(58) Field of Classification Search
CPC ........ A61K 9/0019; A61K 31/197; A61P 1/00
See application file for complete search history.

(56) References Cited

U.S. PATENT DOCUMENTS

| | | | |
|---|---|---|---|
| 8,143,311 | B2 | 3/2012 | Roberts et al. |
| 8,992,891 | B2 | 3/2015 | Cohen et al. |
| 10,813,900 | B2 | 10/2020 | Schmitz et al. |
| 2006/0009523 | A1 | 1/2006 | Trissel et al. |

OTHER PUBLICATIONS

Agarwal et al. "A Pilot Study Assessing Pharmacokinetics and Tolerability of Oral and Intravenous Baclofen in Healthy Adult Volunteers", Journal of Child Neurology 30(1), pp. 37-41 (2015).
Sanchez-Ponce et al., "Metabolic and Pharmacokinetic Differentiation of STX209 and Racemic Baclofen in Humans", Metabolites 2012, 2, 596-613, published Sep. 11, 2012.

*Primary Examiner* — Jessica Worsham
(74) *Attorney, Agent, or Firm* — GREENBLUM & BERNSTEIN, P.L.C.

(57) ABSTRACT

Injectable baclofen formulations and methods that are bioequivalent in terms of plasma baclofen exposure to oral dosage forms but with reduced exposure ratios of baclofen to the M1 metabolite.

12 Claims, No Drawings

COMPOSITIONS AND METHODS OF ADMINISTERING BACLOFEN

CROSS REFERENCE TO RELATED APPLICATIONS

This application is a continuation of U.S. application Ser. No. 17/525,298, filed Nov. 12, 2021. The disclosure of the above-identified application, including the specification, drawings, and claims, is incorporated herein by reference in its entirety.

FIELD

This application relates to, among other things, baclofen formulations, particularly high concentration intramuscular formulations, which improve the ratio of baclofen to metabolites on administration.

BACKGROUND

Baclofen is a widely used anti-spasticity drug and was originally discovered in 1960 by Ciba Geigy. After initial development as a potential antiepileptic agent, it was re-introduced in 1971 as a skeletal muscle relaxant. The original dosage form was an oral tablet and subsequently an intrathecal injection (not for other parenteral routes of administration) and an oral liquid formulation were approved.

Over the last decades, as bioanalytical techniques improved, regulatory agencies have required characterization of major metabolites (typically >10% exposure) of new drugs to better understand and control for metabolite-related pharmacology, toxicology, adverse effects, and drug-drug interactions. In the case of baclofen while the dominant (reported as 15%) metabolite has been identified (3-(4-chlorophenyl)-4-hydroxybutyric acid, hereafter referred to as "metabolite 1," or "M1") and limited evaluation has suggested it is inactive, this does not address its potential full spectrum of potential specific and non-specific biological activity. Additionally, the contribution of the metabolite to the safety, toxicology, or drug-drug interactions remain unknown. Thus while 'generic' forms of baclofen (matching the dosage form and route of administration of already approved baclofen presentations) are assumed to have exactly matching metabolite pharmacokinetics and therefore similar biological effects, this may not be the case for new dosage forms or routes of administration.

The only literature report of M1 pharmacokinetics was a study comparing racemic baclofen tablets (the approved form of baclofen is a racemic 50:50 mix of R- and S-stereoisomers) and the pure R-stereoisomer only. Plasma concentrations of M1 were measured based on pooled 0-12 hour samples, but without no characterization of $C_{max}$, AUC, or $t_{max}$. The study did however identify that M1 metabolite is a result of stereoselective metabolism of only the S-isomer component following racemic baclofen administration.

The only US approved injectable formulation of baclofen is specifically for intrathecal administration and should not be used for other injected routes of administration. There is no information on how different routes of administration affect the amount of metabolite produced.

Still further, there is practically no information about how higher concentrations (e.g., greater than about 2 mg/mL) of injectable baclofen formulations are distributed and processed within the body. In this regard, achieving stable high-concentrations of baclofen, which could be administered without exposing the subject to unacceptably high levels of baclofen degradation products, was not believed possible until relatively recently.

The present invention is based on discoveries made on administering high concentration baclofen formulations through intramuscular administration.

SUMMARY

The invention provides pharmaceutical formulations comprising: an effective amount of 4-amino-3-(4-chlorophenyl)butanoic acid) (baclofen), and one or more pharmaceutically acceptable excipients; wherein the formulation is an injectable formulation; and wherein on administration to a patient produces 3-(4-chlorophenyl)-4-hydroxybutyric acid (M1) as a metabolite in the patient; wherein a ratio $C_{max(baclofen)}:C_{max(M1)}$ is A, and $AUC_{(0-t)(baclofen)}:AUC_{(0-t)(M1)}$ is B; and wherein administering the pharmaceutical formulation to the patient produces A and B values that are more than 10% higher than a ratio $C_{max(baclofen)}:C_{max(M1)}$ and ratio $AUC_{(0-t)(baclofen)}:AUC_{(0-t)(M1)}$ for a baclofen tablet formulation according to Baclofen Tablets monograph as defined by US Pharmacopeia and containing an equal amount of baclofen.

The invention further provides methods of treating spasticity in a patient comprising: administering to the patient a pharmaceutical formulation comprising: an effective amount of 4-amino-3-(4-chlorophenyl)butanoic acid) (baclofen), and one or more pharmaceutically acceptable excipients; wherein the formulation is an injectable formulation; and wherein on administration to a patient produces 3-(4-chlorophenyl)-4-hydroxybutyric acid (M1) as a metabolite in the patient; wherein a ratio $C_{max(baclofen)}:C_{max(M1)}$ is A, and $AUC_{(0-t)(baclofen)}:AUC_{(0-t)(M\,1)}$ is B; and wherein administering the pharmaceutical formulation to the patient produces A and B values that are more than 10% higher than a ratio $C_{max(baclofen)}:C_{max(M1)}$ and a ratio $AUC_{(0-t)(baclofen)}:AUC_{(0-t)(M1)}$ for a baclofen tablet formulation according to Baclofen Tablets monograph as defined by US Pharmacopeia and containing an equal amount of baclofen.

In embodiments, the methods comprise administering the formulation by intramuscular injection. In embodiments, the injectable formulation comprises 4 mg/mL baclofen. In embodiments, intramuscularly administering a 20-mg dose of the formulation to the patient produces a $C_{(max)(baclofen)}$ value of from about 257 ng/mL to about 478 ng/mL. In embodiments, intramuscularly administering a 20-mg dose of the formulation to the patient produces a $C_{(max)(M1)}$ value of from about 30 ng/mL to about 57 ng/mL. In embodiments, intramuscularly administering a 20-mg dose of the formulation to the patient produces a ratio $C_{max(baclofen)}:C_{max(M1)}$ of from about 4.5 to about 15.9, such as from about 8.0 to about 15.9, or from about 8.5 to about 15.9.

In embodiments, intramuscularly administering a 20-mg dose of the formulation to the patient produces a $AUC_{(0-t)(baclofen)}$ value of from about 2017 h·ng/mL to about 2821 h·ng/mL. In embodiments, intramuscularly administering a 20-mg dose of the formulation to the patient produces a $AUC_{(0-t)(M1)}$ value of from about 399 h·ng/mL to about 896 h·ng/mL. In embodiments, intramuscularly administering a 20-mg dose of the formulation to the patient produces a ratio $AUC_{(0-t)(baclofen)}:AUC_{(0-t)(M1)}$ of from about 2.3 to about 7.1, such as from about 3.5 to about 7.1, or from about 3.8 to about 7.1

In embodiments, the spasticity results from multiple sclerosis, and in embodiments, the spasticity is associated with at least one of flexor spasms, pain, clonus, and muscular rigidity. In embodiments, the spasticity results from cerebral palsy, stroke, traumatic brain injury, spinal cord injury, spinal cord disease, or combinations thereof. In embodiments, the effective amount of baclofen is 20 mg.

Additional features, advantages, and further embodiments of the present disclosure will be set forth in part in the description that follows, and in part will be apparent from the description, or may be learned by practice of the present disclosure. The objectives and other advantages of the present disclosure will be realized and attained by means of the elements and combinations particularly pointed out in the description and claims.

The foregoing general description and the following detailed description are exemplary and explanatory only to provide a further explanation of the present disclosure and are not restrictive of the scope of the subject matter encompassed by the claims.

DETAILED DESCRIPTION

The particulars shown herein are by way of example and for purposes of illustrative discussion of the various embodiments of the present disclosure only, and provide what is believed to be the most useful and readily understood description of the principles and conceptual aspects of the disclosed subject matter. In this regard, no attempt is made to show details of the disclosed subject matter in more detail than is necessary for a fundamental understanding of the disclosure, the description making apparent to those skilled in the art how the several forms of the disclosure may be embodied in practice.

The following disclosure refers to more detailed embodiments, with occasional reference to the accompanying figures. The disclosed subject matter, however, may be embodied in different forms and should not be construed as limited to the embodiments set forth herein.

Unless otherwise defined, all technical and scientific terms used herein have the same meaning as commonly understood by one of ordinary skill in the art to which this disclosure belongs. The terminology used in the description herein is for describing particular embodiments only and is not intended to be limiting. As used in the specification and claims, the singular forms "a," "an," and "the" are intended to include the plural forms as well, unless the context clearly indicates otherwise. Also, the phrases "at least one" and "one or more" are intended to be interchangeable, and their use are not intended to limit the scope of any described or claimed feature preceded by "a," "an," and "the" to a singular form.

All publications, patent applications, patents, and other references mentioned herein are expressly incorporated by reference in their entirety, unless otherwise indicated.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and claims are approximations that may vary depending upon the desired properties sought to be obtained by a particular embodiment. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosed subject matter are approximations, the numerical values set forth in the specific examples are reported as precisely as possible. Any numerical value, however, inherently contains certain errors necessarily resulting from the standard deviation found in the method used to obtain the value. Every numerical range given throughout this specification includes every narrower numerical range that falls within such broader numerical range, as if such narrower numerical ranges were all expressly written herein.

Reference to compounds in the specification includes esters and salts of such compounds. Thus, even if not explicitly disclosed, such esters and salts are contemplated and encompassed by reference to the compounds themselves.

All percent measurements in this application, unless otherwise stated, are measured by weight based upon 100% of a given sample weight. Thus, for example, 30% represents 30 weight parts out of every 100 weight parts of the sample.

The present disclosure relates, in part, to a composition comprising an active ingredient, and a stabilizer. The composition may be a pharmaceutical composition.

A "pharmaceutical composition" as used herein means a composition comprising an active ingredient and at least one pharmaceutically acceptable excipient. As used herein, the term "pharmaceutically acceptable excipient" means a compound or ingredient that is compatible with the other ingredients in a pharmaceutical formulation and not injurious to an intended subject when administered in normal or therapeutically effective amounts. As used herein, an "intended subject" includes animals and/or humans. The terms "patient" and "subject" may be used interchangeably.

Suitable excipients are known to those of skill in the art and examples are described, for example, in the Handbook of Pharmaceutical Excipients (Kibbe (ed.), 3rd Edition (2000), American Pharmaceutical Association, Washington, D.C.), and Remington's Pharmaceutical Sciences (Gennaro (ed.), 20th edition (2000), Mack Publishing, Inc., Easton, Pa.), which, for their disclosures relating to excipients and dosage forms, are incorporated herein by reference. Examples of excipients include but are not limited to fillers, extenders, diluents, wetting agents, solvents, emulsifiers, preservatives, absorption enhancers, sustained-release matrices, starches, sugars, microcrystalline cellulose, granulating agents, lubricants, binders, disintegrating agents, coloring agents, release agents, coating agents, sweetening agents, flavoring agents, perfuming agents, antioxidants, plasticizers, gelling agents, thickeners, hardeners, setting agents, suspending agents, surfactants, humectants, carriers, stabilizers, and combinations thereof.

The present disclosure includes a large number and variety of components that are contemplated for inclusion in the pharmaceutical formulations. It should be recognized that when the inventors expressly contemplate including such components, they also expressly contemplate excluding such components. Thus, all components disclosed herein are expressly contemplated for exclusion as well.

As used herein, "active ingredient" is any component of the composition intended to furnish pharmacological activity or other direct effect in the diagnosis, cure, mitigation, treatment, or prevention of disease, or to affect the structure or any function of the body of the intended subject. Active ingredients include those components of the composition that may undergo chemical change during the manufacture of the composition and be present in a finished composition in a modified form intended to furnish the specified activity or effect. Active ingredients also include those components of the finished composition that during or after administration of the finished drug product to the intended user may undergo chemical change to a modified form intended to furnish the specified activity or effect. For example, the active ingredient can be a pharmaceutically acceptable salt of the component that furnishes the specified activity or effect.

As used herein, the term "pharmaceutically acceptable salt" includes salts that are physiologically tolerated by the intended subject. Such salts are typically prepared from an inorganic and/or organic acid. Examples of suitable inorganic acids include hydrochloric, hydrobromic, hydroiodic, nitric, sulfuric, and phosphoric acid. Organic acids may be aliphatic, aromatic, carboxylic, and/or sulfonic acids. Suitable organic acids include formic, acetic, propionic, succinic, camphorsulfonic, citric, fumaric, gluconic, lactic, malic, mucic, tartaric, para-toluenesulfonic, glycolic, glucuronic, maleic, furoic, glutamic, benzoic, anthranilic, salicylic, phenylacetic, mandelic, pamoic, methanesulfonic, ethanesulfonic, pantothenic, benzenesulfonic (besylate), stearic, sulfanilic, alginic, galacturonic, and the like.

The composition may contain only one active ingredient, or more than one active ingredient, such as two, three, four, five, six, seven, eight, or nine active ingredients, or more than nine active ingredients.

The active ingredient can be selected from among active pharmaceutical ingredients (APIs). An API is a substance or mixture of substances intended to be used in the manufacture of a pharmaceutical product and that, when used in the production of a pharmaceutical product, becomes an active ingredient of the pharmaceutical product. Such substances are intended to furnish pharmacological activity or other direct effect in the diagnosis, cure, mitigation, treatment, or prevention of disease or to affect the structure or function of the body of the intended subject.

In some embodiments, the active ingredient is a lactam-forming ingredient, such as a 4-amino-3-substituted-butanoic acid derivative. Examples of 4-amino-3-substituted-butanoic acid derivatives include baclofen, gabapentin, and pregabalin.

In some embodiments, the active ingredient is selected from baclofen (4-amino-3-(4-chlorophenyl)butanoic acid) and its pharmaceutically acceptable salts.

Baclofen as used herein refers to (4-amino-3-(4-chlorophenyl)butanoic acid), enantiomers, racemic mixtures, polymorphs, salts, solvates, esters, or hydrates thereof. Baclofen includes R-baclofen (D-baclofen), S-baclofen (L-baclofen), or their mixtures including the racemate. The racemate refers to a mixture of R and S-baclofen (DL-baclofen) in equal proportions.

Specifically contemplated salts of baclofen include salts of acidic or basic groups present in compounds of the application. Pharmaceutically acceptable acid addition salts of baclofen include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, or pamoate salts. Certain compounds of the invention can form pharmaceutically acceptable salts with various amino acids. Suitable base salts include, but are not limited to, aluminum, calcium, lithium, magnesium, potassium, sodium, zinc, or diethanolamine salts. Potassium salts include potassium chloride, potassium bicarbonate, potassium phosphate, gluconate, potassium citrate, or the like.

Baclofen has the following structure:

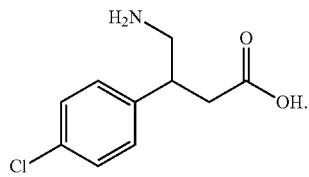 [SMILES: NCC(CC(=O)O)c1ccc(Cl)cc1]

Formulations

As used herein, a formulation for use as an injectable composition comprises a fluid composition. Typically, the formulation comprising baclofen can be used for injection and is a fluid composition at room temperature and at body temperature of the subject in which the formulation is used. Fluid compositions include solutions, suspensions, dispersions, or the like. Preferably, the fluid composition is a solution that is essentially free or free from particles or particulates that can be observed on visual inspection. The term "particulate" includes mobile undissolved particles, other than gas bubbles, unintentionally present in the drug solution.

While the fluid compositions may contain any of a number of known pharmaceutical additives or excipients, in many embodiments, the fluid compositions contain as few ingredients or components as possible to achieve a desired pH, stability (low 4-(4-chlorophenyl)-2-pyrrolidone, hereinafter "4-CPP"), concentration, and tonicity or ionic strength.

Preferably, the fluid composition has a pH of between 5.0 and 7.5, such as between 5.5 and 6.5, or about 6.0. For example, the pH can be about 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5.

Preferably, the fluid composition has a concentration of 4-CPP of 1.3% or less (based on the starting concentration of baclofen), such as about 1% 4-CPP or less, or about 0.6% 4-CPP or less. For example, in some embodiments, the level of 4-CPP in the terminally sterilized solution is less than about 1.2%, 1.1%, 1.0%, 0.9%, 0.8%, 0.7%, 0.6%, 0.5%, 0.4%, 0.3%, 0.2%, 0.1%, 0.05%, 0.025%, or lower.

In some embodiments, the current application provides reduced amounts of 4-(4-chlorophenyl)-2-pyrrolidinone (4-CPP) in a terminally sterilized injectable baclofen formulation, produced by a method comprising: adjusting a pH of baclofen in an aqueous solvent to between about 4.0 and about 6.2 to form a pH adjusted solution, the aqueous solvent comprising water, a saline solution, water containing phosphate, sulfate, potassium, magnesium or a saline solution containing sulfate, phosphate, potassium or magnesium, wherein the concentration of baclofen in the aqueous solvent is between 0.05 mg/mL and 10 mg/mL; and steam sterilizing the pH adjusted solution to achieve a sterility assurance level of $1 \times 10^6$ so as to form a terminally sterilized solution having a pH of between about 5.0 and about 7.5, the terminally sterilized solution having less than 1.0% of 4-CPP based on the concentration of baclofen added to the aqueous solvent.

In some embodiments, the present application provides baclofen formulations having low 4-CPP concentrations produced by controlling the pH of the baclofen solution prior to steam sterilization, where the pH is in the range of between about 4.0 to about 7.0, the amount of 4-CPP formed is reduced, when the pH is raised to between about 5.0 to about 7.0 after heat sterilization. In some embodiments, the 4-CPP impurity levels are low at a pH of between about 4.0 to about 4.5.

The present baclofen formulations and compositions may be produced in a variety of ways, with specific methods provided in U.S. Pat. No. 10,813,900, which is incorporated by reference for its disclosure of methods of manufacturing baclofen compositions and formulations.

The formulation may have any suitable ionic strength. The formulation may include a salt, such as NaCl or KCl, to maintain ionic strength. In various embodiments, the combined ionic strength of the formulation contributed by the various components of the formulation, such as baclofen, and one or more salts is the equivalent of the ionic strength of between about 0.1 M and 0.2 M NaCl or KCl, or about 0.15 M NaCl or KCl. For example, 25 mM $Na_3PO_4$ buffer solution may include 0.085 M NaCl or KCl to yield a combined ionic strength of the buffer and the NaCl or KCl at an equivalent of 0.15 M NaCl (e.g., about 0.154 M NaCl or KCl), which is substantially isotonic with CSF.

In embodiments where the formulation is to be delivered to a central nervous system of a subject, it may be desirable for the formulation to be isotonic with cerebrospinal fluid, which typically has a tonicity of about 305 mOsm. For purposes of the present disclosure, a formulation having a tonicity of between about 270 mOsm and 315 mOsm, e.g., between about 285 mOsm and 315 mOsm is considered to be isotonic with cerebrospinal fluid. For intramuscular formulations, tonicity may be between, for example, 280 and 310 mOsm. While such tonicities are desired, the overall ionic strength of the formulation may, in many cases, take precedence over the desire to achieve isotonicity.

In various embodiments, injectable baclofen solutions include sulfate or phosphate. As used herein, "sulfate" refers to $SO_4^{2-}$ or $HSO_4^-$. As used herein, "phosphate" refers to $PO_4^{3-}$, $HPO_4^{2-}$, or $H_2PO_4^-$. It will be understood that when in water the various species of sulfate or phosphate will be in equilibrium. When a concentration of sulfate or phosphate is used herein, the concentration will refer to the total concentration of all of the various species of sulfate or phosphate present. Sulfate or phosphate may result from dissolving an appropriate acid or salt of sulfate or phosphate in the solution. In many embodiments, sulfate is derived from $Na_2SO_4$. In embodiments, the phosphate is derived from $NaH_2PO_4$. For its discussion of the use of sodium sulfate and sodium phosphate (esp. sodium dihydrogen phosphate dihydrate), U.S. Pat. No. 9,597,304 is incorporated by reference. The concentration of such buffer solutions will desirably balance long-term storage and physiological acceptability. A range of from about 5 mM to 25 mM concentration may be desirable.

It has been found that the solubility of baclofen is increased in solutions comprising sulfate or phosphate. As discussed in more details in the Examples that follow, it has been found that concentrations greater than 2 mg/mL, such as greater than 3 mg/mL, greater than 4 mg/mL, greater than 5 mg/mL, or greater than 6 mg/mL baclofen can be dissolved in solutions containing phosphate, sulfate, potassium, sodium, or magnesium. A concentration of 8.8 mg/mL sodium chloride is considered isotonic and therefore desirable as being physiologically acceptable.

In some embodiments, the present application provides stable aqueous baclofen solutions at concentrations greater than the 2.0 mg/mL, and methods of their administration. In particular, in some embodiments, the present application provides stable aqueous baclofen solutions having concentrations greater than about 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, or 7.0 mg/mL.

In some embodiments, the present application provides stable aqueous baclofen solutions having concentrations less than about 7.5, 8.0, 8.5, 9.0, 9.5, 10.0, 10.5, 11.0, 11.5 or 12.0 mg/mL. The term "stable," as used herein, is meant to describe a compound, composition, or other substance that retains its properties without loss of potency and maintains its physical characteristics over time with minimal degradation.

In some embodiments, the concentration of phosphate or sulfate is from 5 mM to 25 mM. At concentrations above 25 mM, the phosphate or sulfate may provide the solution with sufficient ionic strength such that no ionic strength enhancing agent is added to increase the ionic strength. If the resultant solution has an ionic strength less than about 0.15 M NaCl, an ionic strength enhancing agent such as NaCl may be added to produce a suitable ionic strength.

In various embodiments, the fluid composition containing baclofen is an injectable baclofen solution. The solution, in embodiments, includes (i) baclofen in a concentration greater than 2 mg/mL; and (ii) sulfate or phosphate in a concentration of from 5 mM to 25 mM. The solution may have an ionic strength equivalent of between 0.14 M NaCl and 0.16 M NaCl. In some embodiments, the solution consists essentially of the baclofen, the sulfate (e.g., from $Na_2SO_4$) or phosphate (e.g., from $NaH_2PO_4$), sodium ion, and water. In embodiments, the solution consists essentially of the baclofen, the sulfate or phosphate, sodium, ion, chloride ion (e.g., from NaCl), and water.

A preferred composition for IM injection includes 4 mg/mL baclofen, 8.2 mg/mL sodium chloride, 1.6 mg/mL sodium dihydrogen phosphate dihydrate, and 992 mg/mL water, with the pH adjusted to about 5.6-5.7 with sodium hydroxide.

Preparation

Any appropriate form of baclofen can be used to prepare the formulations of the present application. In some embodiments, appropriate forms of baclofen include baclofen solids such as powdered, lyophilized, or microfluidized baclofen. In some embodiments, the baclofen can be provided as aqueous or non-aqueous solutions of baclofen, including buffered solutions, where pharmaceutically undesirable components of the solution are either diluted to pharmaceutically-acceptable levels or removed from the final baclofen formulation prior to pharmaceutical administration. In some embodiments, the baclofen that can be used in the formulation comprises amorphous baclofen.

Fluid compositions comprising baclofen as described herein may be prepared in any suitable manner. Preferably the fluid compositions are sterilized. As used herein, "sterilized" means essentially free or free of microorganisms (e.g., bacteria, viruses, fungi, etc.) and their spores. Often sterility assurances of a $1\times10^6$ reduction are required to claim terminal sterility. In various embodiments the compositions are sterilized by heat treatment, such as steam sterilization or autoclaving. In some embodiments, heat treatment, regardless of temperature, time, or type, which results in a $1\times10^6$ sterility assurance level (the probability that a given unit is not sterile is one in a million) is used. In some embodiments, the fluid compositions are sterilized to an F0 for at least 15 minutes at 121° C.

Heat sterilization, however, can result in increased production of 4-CPP. As discussed below in more detail in the Examples in U.S. Pat. No. 10,813,900, it has been found that adjusting the pH to a pH lower than the ultimate desired pH can result in less 4-CPP production following heat treatment. It has also been found that the pH tends to increase following heat treatment. Accordingly, a baclofen composition may be pH adjusted to a pH less than the ultimately desired pH and then heat sterilized to produce a low 4-CPP composition with a desired long term pH.

In various embodiments, preparing a terminally sterilized injectable baclofen formulation suitable for injection into cerebrospinal fluid of a patient includes (i) dissolving baclofen in aqueous solvent to generate an initial solution, wherein the concentration of baclofen in the initial solution is between 0.05 mg/mL and 7 mg/mL; (ii) adjusting the pH of the initial solution to between 5.0 and 6.2 to produce a pH adjusted solution; and (iii) steam sterilizing the pH adjusted solution to an F0 for at least 15 minutes at 1210° C. to produce a terminally sterilized solution, wherein the terminally sterilized solution, after storage of 30 days at room temperature, has a pH of between 5.0 and 7.0 and less than 1.3% of 4-(4-chlorophenyl)-2-pyrrolidinone (4-CPP) based on the concentration of baclofen added to the initial solution. In some embodiments, the terminally sterilized solution, after storage of 30 days at room temperature, has less than about 1% 4-CPP.

In some embodiments, the aqueous solvent is preferably water, a saline solution (which, as used herein, means a solution consisting of or consisting essentially of water and dissolved sodium chloride), a sulfate or phosphate solution (which, as used herein, means a solution consisting of or consisting essentially of water and dissolved sulfate or phosphate salt or acid), or a sulfate or phosphate saline solution (which, as used herein, means a solution consisting of or consisting essentially of water and dissolved sodium chloride and dissolved sulfate or phosphate salt or acid).

The terminally sterilized injectable baclofen formulation may have any suitable concentration of baclofen, such as between 0.01 mg/mL and 10 mg/mL baclofen. In embodiments, the terminally sterilized injectable baclofen formulation has between 0.05 mg/mL and 2 mg/mL baclofen.

The pH may be adjusted with any suitable acid or base. In embodiments, the pH is adjusted with HCl, $H_2SO_4$, $H_3PO_4$, or NaOH.

In embodiments, the terminally sterilized injectable baclofen formulation has an ionic strength equivalent to about 0.14 M NaCl to about 0.16 M NaCl, such as about 0.15 M NaCl. NaCl may be added to achieve a desired ionic strength.

In embodiments, the terminally sterilized solution, after storage of 30 days at room temperature, has a pH of between 5.5 and 6.7, such as about 6.0.

In embodiments, the concentration of baclofen in the initial solution is about 0.05 mg/mL, and the pH is adjusted to between 5.0 and 5.5.

In embodiments, the concentration of baclofen in the initial solution is about 0.5 mg/mL, and the pH is adjusted to between 5.5 and 6.2.

In embodiments, the concentration of baclofen in the initial solution is about 2 mg/mL, and the pH is adjusted to between 5.5 and 6.2.

In embodiments, the initial solution consists essentially of baclofen, dissolved NaCl or KCl, and water.

As mentioned above, U.S. Pat. No. 10,813,900 describes methods for producing baclofen compositions and formulations that are suitable for use in the methods of the present invention. However, the inventors believe the pharmacokinetic phenomena observed with this invention does not relate necessarily to the method of manufacturing the composition, but rather to the route of administration. The basis for these conclusions is clear from the Examples below.

Administration

Formulations according to the present disclosure may be administered to a subject through any acceptable route. For example, the fluid formulations may be administered intravenously, subcutaneously, intramuscularly, intra-arterially, intrathecally, epidurally, intraparenchymally, intraperitoneally, intracerebroventricularly, intaventically, etc., by infusion or injection. Intramuscular is the preferred route.

Preferably, a therapeutically effective dose of baclofen is administered to a patient in need of treatment. By "therapeutically effective dose" herein is meant a dose that produces the effects for which it is administered. The exact dose will depend on the purpose of the treatment, and will be ascertainable by one skilled in the art using known techniques. In some embodiments, dosages of about 0.5 micrograms/kg to about 5 micrograms/kg are used. As is known in the art, adjustments for systemic versus localized delivery, and rate of new protease synthesis, as well as the age, body weight, general health, gender, diet, time of administration, drug interaction and the severity of the condition may be necessary, and will be ascertainable with routine experimentation by those skilled in the art.

In some embodiments, baclofen is delivered to a patient in a daily dose of between about 0.001 mg/kg/day to 100 mg/kg/day. A "patient" for the purposes of the present disclosure includes both humans and other animals, particularly mammals including mice, rats, guinea pigs, rabbits, dogs, cats, swine, bovine, monkey, baboon, chimpanzee, and other organisms. Thus, the methods are applicable to both human therapy and veterinary applications. In a preferred embodiment the patient is a mammal, such as a human. Those "in need of treatment" include mammals already having the disease or disorder, as well as those prone to having the disease or disorder, including those in which the disease or disorder is to be prevented.

The baclofen formulations of the current application allows for subsequent dilution by the addition of other components that are to be simultaneously infused or injected with the baclofen. These include pain relieving medications suitable for combination with the baclofen and include morphine, clonidine, hydromorphine, hydrocodone, meperidine, celecoxib, tramadol, oxycodone, acetaminophen, ketoprofen, ketorolac, ibuprofen, naproxen, or the like. It is appreciated in the art that other chemical compounds are similarly suitable for co-administration or separate administration with baclofen in the current application.

The stable baclofen formulations of the present application can be provided in a medical package of baclofen solution suitable for injection. In some embodiments, the medical package contains a solution that is compatible with the desired site of administration (e.g., cerebrospinal fluid suitable for intrathecal administration). In some embodiments, the baclofen formulation will be provided in a sterile, isotonic solution of baclofen free of pyrogens, antioxidants, preservatives, or other potentially neurotoxic additives.

The baclofen formulations of the present application can be packaged in a pre-filled container, such as an ampule, vial, or syringe that is ready for immediate delivery by injection or to an infusion device. The packaging may include, for example, a syringe with a luer-lock tip filled with the baclofen, a color-coding system (label) for the various concentrations of the drug product and size of syringe, a package, a label, and instructions for use. The packaging may include, for example, a sealed ampule or vial within a package, a label, and instructions. The term "prefilled," as used herein, means containing an exact, predetermined dose of a sterile pharmaceutical composition.

Pharmacology and Indications

Baclofen is a 4-amino-3-substituted-butanoic acid derivative and a structural analog of the inhibitory neurotransmitter gamma-aminobutyric acid (GABA), and may exert its effects by stimulation of the GABAB receptor subtype. Baclofen is a skeletal muscle relaxant and antispastic agent. Baclofen is useful for the alleviation of signs and symptoms of spasticity resulting from multiple sclerosis, particularly for the relief of flexor spasms and concomitant pain, clonus, and muscular rigidity. Baclofen may also be used for the treatment of spasticity and/or other conditions related to Cerebral Palsy, Stroke, Traumatic Brain Injury, Spinal Cord Injury, and Spinal Cord Diseases. In stroke patients, baclofen should be used with caution; in some patients, baclofen has not significantly benefited stroke patients, and in others, it is not well tolerated. Baclofen has also been used as a withdrawal treatment for patients that are resistant to, or otherwise cannot take, benzodiazepines. The inventors contemplate that baclofen formulations according to the invention may be used for any indication for which baclofen is approved in any country around the world, as well as indications that are not approved by regulatory bodies but remain in use by physicians. Uses for baclofen include, for example, alcohol withdrawal, chronic hiccups, cocaine addiction, GERD, and gastroparesis.

The amount of the dose of the active ingredient administered, as well as the dose frequency, will vary depending on the particular dosage form used and route of administration. The amount and frequency of administration will also vary according to the age, body weight, and response of the individual subject or patient. Typical dosing regimens can readily be determined by a competent physician without undue experimentation. It is also noted that the clinician or treating physician will know how and when to interrupt, adjust, or terminate therapy in conjunction with individual subject or patient response.

In general, the total daily dosage for treating, preventing, and/or managing the conditions associated with spasticity with any of the formulations according to the present disclosure is from about 1 mg to about 500 mg, or about 1, 5, 10, 15, 20, 25, 30, 35, 40, 45, 50, 55, 60, 70, 80, 90, 100, 120, 140, 150, 160, 180, 200, 250, 300, 350, 400, 450, or 500, mg, or any number in between, of baclofen, a derivative thereof, or a pharmaceutically acceptable salt thereof. Other indications may require higher doses, such as 600, 700, 800, 900, or even 1000 mg. For example, for an orally administered dosage form, the total daily dose may range from about 10 mg to about 100 mg, or from about 20 mg to about 90 mg, or from about 30 mg to about 80 mg, or from about 40 mg to about 70 mg. Accordingly, a single oral dose may be formulated to contain about 1, 5, 10, 15, 20, 25, 30, 35, 40, 45, 50, 55, 60, 70, 80, 90, 100, 120, 140, 150, 160, 180, or 200, mg, or any number in between, of baclofen, a derivative thereof or a pharmaceutically acceptable salt thereof. The pharmaceutical compositions containing baclofen, a derivative thereof or a pharmaceutically acceptable salt thereof may be administered in single or divided doses 1, 2, 3, 4, or more times each day. Alternatively, the dose may be delivered once every 2, 3, 4, 5, or more days. In one embodiment, the pharmaceutical compositions are administered once per day.

As used herein, the term "prevent" or "prevention" in the context of treatment, for example, as in "preventing spasticity" or "prevention of spasticity" refers to a reduction in the spasticity. Prevention does not require 100% elimination of the symptom.

Embodiments of the invention include pharmaceutical formulations comprising: an effective amount of 4-amino-3-(4-chlorophenyl)butanoic acid) (baclofen), and one or more pharmaceutically acceptable excipients; wherein the formulation is an injectable formulation; and wherein on administration to a patient produces 3-(4-chlorophenyl)-4-hydroxybutyric acid (M1) as a metabolite in the patient; wherein a ratio $C_{max(baclofen)}:C_{max(M1)}$ is A, and $AUC_{(0-t)(baclofen)}:AUC_{(0-t)(M1)}$ is B; and wherein administering the pharmaceutical formulation to the patient produces A and B values that are greater than 10% higher than a ratio $C_{max(baclofen)}:C_{max(M1)}$ and $AUC_{(0-t)(baclofen)}:AUC_{(0-t)(M1)}$ for a baclofen tablet formulation according to Baclofen Tablets monograph as defined by US Pharmacopeia and containing an equal amount of baclofen. Methods of administering such formulations are contemplated and disclosed.

In the context above, with respect to the invention producing ratios that are greater than 10% higher than a reference value, this can be calculated or determined as follows. First, the reference ratio is determined; the 10% value of that ratio is calculated; the 10% value is added to the reference ratio; and the inventive compositions would produce ratios that are above the reference ratio plus its 10% value.

In embodiments, administering a 20-mg dose of a 4 mg/mL concentration of the pharmaceutical formulation to the patient produces a $C_{(max)(baclofen)}$ value of from about 257 ng/mL to about 478 ng/mL. In embodiments, administering a 20-mg dose of a 4 mg/mL concentration of the pharmaceutical formulation to the patient produces a $C_{(max)(M1)}$ value of from about 30 ng/mL to about 57 ng/mL. In embodiments, administering a 20-mg dose of a 4 mg/mL concentration of the pharmaceutical formulation to the patient produces a ratio $C_{max(baclofen)}:C_{max(M1)}$ of from about 4.5 to about 15.9, such as from about 8.0 to about 15.9, or from about 8.5 to about 15.9.

In embodiments, administering a 20-mg dose of a 4 mg/mL concentration of the pharmaceutical formulation to the patient produces a $AUC_{(0-t)(baclofen)}$ value of from about 2017 h·ng/mL to about 2821 h·ng/mL. In embodiments, administering a 20-mg dose of a 4 mg/mL concentration of the pharmaceutical formulation to the patient produces a $AUC_{(0-t)(M1)}$ value of from about 399 h·ng/mL to about 896 h·ng/mL. In embodiments, administering a 20-mg dose of a 4 mg/mL concentration of the pharmaceutical formulation to the patient produces a ratio $AUC_{(0-t)(baclofen)}:AUC_{(0-t)(M1)}$ of from about 2.3 to about 7.1, such as from about 3.5 to about 7.1, or from about 3.8 to about 7.1.

In embodiments, the method provides for treating spasticity resulting from multiple sclerosis. In embodiments, the method provides for treating spasticity associated with at least one of flexor spasms, pain, clonus, and muscular rigidity. In embodiments, the effective amount of baclofen is from about 5 mg to about 20 mg, and can be administered in divided or single doses, such as four 5-mg doses taken together, two 10-mg doses taken together, one 20-mg dose, a divided 40-mg dose, etc. Embodiments include, for example, gradually increasing the dosing regimen where 5 mg to 20 mg dosing is taken more than once per day, such as for example, three times a day. For example, embodiments include administering the baclofen as a 5-mg dose three times daily for three days; then increasing to 10 mg three times daily for three days; then increasing to 20 mg three times daily for three days. Additional increases may be necessary up to the maximum recommended dosage. Obviously, qualified medical practitioners can modify this regimen as necessary, including by increasing or decreasing the daily frequency, or increasing or decreasing the number of days at each dose, etc.

EXAMPLES

The inventors compared the pharmacokinetics of IM baclofen formulations to a reference baclofen tablet formulation. The details are provided in the Examples below.

Example 1—Dose Finding and Tolerability: Intramuscular Baclofen First-In-Humans

Prior to initiating a pivotal study to support the potential approval of intramuscular baclofen by the FDA, the inventors wanted to better understand the tolerability and initial pharmacokinetics of intramuscular baclofen in a smaller set of patients and at a variety of doses. To conduct this assessment, the inventors conducted an open-label, non-randomized study described below.

Overall Study Design

This was an open-label, non-randomized study in which 3 consecutive doses were administered to healthy volunteers (subjects) under fasting conditions. Multiple measurements and safety assessments were conducted in addition to pharmacokinetic (PK) measurements.

During period 1, subjects were recruited and were administered a single, 20 mg dose of Baclofen Oral Tablets. These subjects then had their blood drawn for a series of analyses. Following administration and 24 hours of blood sample collection, patients were released from the clinic for a 14-day washout period.

Subjects were then asked to return for Period 2. In Period 2, subjects administered 12 mg (3 ml) of 4 mg/ml Baclofen Intramuscular Injection. Following the injection, patients remained at the clinic for 48 hours, during which, patients received the same set of blood draws. Following that, patients were released from the clinic for a 14-day washout. After receiving the data comparing Period 2 to Period 1 and confirming the safety and tolerability of the 3 ml volume of injection, the inventors then selected a $3^{rd}$ dose.

The inventors were surprised by the data as they were expecting the results of Period 2 to suggest a $3^{rd}$ dose (the target dose to match the PK parameters of the 20 mg Oral Baclofen Tablet) that was below 20 mg of intramuscular baclofen injection as was previously reported using intravenous baclofen. Instead, the data suggested that intramuscular and oral baclofen have a pharmacokinetic profile that approaches a 1:1 drug exposure despite direct injection.

The inventors then selected 20 mg (5 ml) as the dose for the subject in Period 3. During Period 3, the same subject were asked to return to the clinic for a $3^{rd}$ set of dosing. Each returning subject was given 20 mg (5 ml) of baclofen intramuscular injection. Following injection, the subjects remained at the clinic for 48 hours and then were released.

The study provided a good basis of information as it supported the viability of intramuscular baclofen from a safety standpoint, although the volume of the injection was significant. The study also provided important information related to dose selection based on the PK parameters measured. The study, however, had several challenges as it related to interpreting the information. First, the subjects were not randomized. Second, the subjects all received the same treatment in the same order on the same days.

Lab values were generally obtained from using similar methods to those described in more detail in Example 2. Data below summarize the results of the data collected in the study.

Pharmacokinetic Analysis

The PK parameters calculated for baclofen and baclofen M1 were $AUC_{0-t}$, $AUC_{0-\infty}$, $C_{max}$, $t_{max}$, $\lambda_z$, and $t_{1/2}$. The PK values for the IM and oral tablet treatments (baclofen and M1) are summarized in the tables below.

The following tables summarize parameters for baclofen.

| Pharmacokinetic Parameters of Oral Baclofen (20 mg Tablet) | | | | | | |
|---|---|---|---|---|---|---|
| Mean Parameters (+/−SD) | | | | | | |
| | $C_{max}$ (ng/mL) | $T_{max}$* (h) | $AUC_{0-t}$ (h*ng/mL) | $AUC_{0-\infty}$ (h*ng/mL) | $T_{1/2}$ (h) | $\lambda_z$ (/h) |
| N = 14 Subjects | 373.01 (+/−111.83) | 0.994 (0.740, 2.988) | 2139.87 (+/−217.40) | 2160.57 (+/−221.84) | 5.38 (+/−0.87) | 0.1322 (+/−0.0223) |

| Pharmacokinetic Parameters of 12 mg Intramuscular Baclofen (4 mg/ml injection) | | | | | | |
|---|---|---|---|---|---|---|
| Mean Parameters (+/−SD) | | | | | | |
| | $C_{max}$ (ng/mL) | $T_{max}$* (h) | $AUC_{0-t}$ (h*ng/mL) | $AUC_{0-\infty}$ (h*ng/mL) | $T_{1/2}$ (h) | $\lambda_z$ (/h) |
| N = 14 Subjects | 224.89 (+/−53.24) | 0.736 (0.239, .991) | 1474.13 (+/−146.28) | 1494.34 (+/−142.72) | 5.24 (+/−0.78) | 0.1350 (+/−0.0205) |

| Pharmacokinetic Parameters of 20 mg Intramuscular Baclofen (4 mg/ml injection) | | | | | | |
|---|---|---|---|---|---|---|
| Mean Parameters (+/−SD) | | | | | | |
| | $C_{max}$ (ng/mL) | $T_{max}$* (h) | $AUC_{0-t}$ (h*ng/mL) | $AUC_{0-\infty}$ (h*ng/mL) | $T_{1/2}$ (h) | $\lambda_z$ (/h) |
| N = 14 Subjects | 340.70 (+/−51.74) | 0.743 (0.236, .993) | 2482.3 (+/−259.74) | 2502.92 (+/−261.25) | 5.45 (+/−0.86) | 0.1299 (+/−0.0190) |

The results in the table above are surprising and unexpected. The inventors expected the Period 3 dosing to be less than 20 mg. The actual result is in contrast to the results reported by Agarwal et al. in *Journal of Child Neurology* 30(1), p. 37-41 (2015) (a study of 12 subjects, 9 male and 3 female, of age 26-56), which reported a bioavailability ($AUC_{0-\infty}$) of about 75% of an oral tablet dose compared to an IV dose. Agarwal et al.'s study would lead to reduced IV dosing relative to oral dosing (based on higher bioavailability for the IV dose); the present study would suggest approximately 1:1 dosing for IM compared to oral.

A difference in bioavailability for an oral dosage relative to an injected dosage—with the oral dosage resulting in lower bioavailability of the administered drug—as demonstrated by Agarwal et al. is not surprising. Many orally administered drugs are either poorly absorbed from the gastrointestinal tract, or are metabolized by the liver after being absorbed from the GI (the so-called "first pass effect"). The relatively comparable bioavailability observed in the present study for the IM versus oral administration is surprising for this reason as well. It is not clear why this result is occurring.

The following tables summarize parameters for M1.

It was notable and unexpected to the inventors that the dosing requirement was consistent with that of oral baclofen tablets but the pharmacokinetic ratios noted above were not.

Example 2—Pharmacokinetics: Intramuscular Baclofen Versus Oral Baclofen Tablet

Overall Study Design

This was an open-label, randomized, two-way crossover, single-dose study comparing the bioavailability and pharmacokinetics (PK) of baclofen administered by an IM injection and an oral tablet dose in healthy volunteers (subjects) under fasting conditions.

During Period 1, subjects were randomized to receive either a single dose (20 mg) of either Baclofen Oral Tablets or Baclofen IM Injection (4 mg/mL for a total dose of 20 mg [5 mL]) on Study Day 1, followed by a series of blood draws for PK analysis at the following timepoints: at pre-dose (0.000), 5, 15, 30 and 45 minutes and at 1.00, 2.00, 3.00, 4.00, 6.00, 8.00, 10.0, 12.0, 24.0, 36.0, and 48.0 hours post-dose. Subjects were released from the clinic after the 24-hour blood draw. Subjects returned to the clinic on the Pharmacokinetic Parameters of M1: Oral Baclofen (20 mg Tablet)

Mean Parameters (+/−SD)

| | $C_{max}$ (ng/mL) | $T_{max}$* (h) | $AUC_{0-t}$ (h*ng/mL) | $AUC_{0-\infty}$ (h*ng/mL) | $T_{1/2}$ (h) | $\lambda_z$ (/h) |
|---|---|---|---|---|---|---|
| N = 14 Subjects | 55.22 (+/−14.74) | 3.996 (2.998, 5.991) | 754.95 (+/−272.88) | 783.33 (+/−279.52) | 8.33 (+/−2.05) | 0.0886 (+/−0.0240) |

Pharmacokinetic Parameters of M1: 12 mg Intramuscular Baclofen (4 mg/ml injection)

Mean Parameters (+/−SD)

| | $C_{max}$ (ng/mL) | $T_{max}$* (h) | $AUC_{0-t}$ (h*ng/mL) | $AUC_{0-\infty}$ (h*ng/mL) | $T_{1/2}$ (h) | $\lambda_z$ (/h) |
|---|---|---|---|---|---|---|
| N = 14 Subjects | 26.01 (+/−7.94) | 5.987 (3.986, 7.953) | 423.92 (+/−160.28) | 450.46 (+/−168.07) | 9.32 (+/−2.94) | 0.0835 (+/−0.0326) |

Pharmacokinetic Parameters of M1: 20 mg Intramuscular Baclofen (4 mg/ml injection)

Mean Parameters (+/−SD)

| | $C_{max}$ (ng/mL) | $T_{max}$* (h) | $AUC_{0-t}$ (h*ng/mL) | $AUC_{0-\infty}$ (h*ng/mL) | $T_{1/2}$ (h) | $\lambda_z$ (/h) |
|---|---|---|---|---|---|---|
| N = 14 Subjects | 47.40 (+/−13.63) | 5.988 (3.991, 6.002) | 814.41 (+/−322.91) | 854.28 (+/−341.55) | 9.28 (+/−2.86) | 0.0815 (+/−0.0249) |

Ratios for the $C_{max(baclofen)}$:$C_{max(M1)}$ and $AUC_{(0-t)(baclofen)}$:$AUC_{(0-t)(M1)}$ can easily be calculated from the information in the tables above. For example, for the IM 12 mg administration, the $C_{max}$ value for baclofen ($C_{max(baclofen)}$) is 224.89; the $C_{max}$ value for M1 ($C_{max(M1)}$) is 26.01; accordingly, 224.89/26.01 is 8.64, or 8.6 rounded down. Calculated ratios are shown in the table below.

| Treatment | $C_{max(baclofen)}$:$C_{max(M1)}$ | $AUC_{(0-t)(baclofen)}$:$AUC_{(0-t)(M1)}$ |
|---|---|---|
| IM 12 mg | 8.6 | 3.5 |
| IM 20 mg | 7.2 | 3.0 |
| Oral tablet | 6.8 | 2.8 | evening of Day 2 for the collection of the 36 hour post-dose PK blood draw. Subjects returned to the clinic on the morning of Day 3 for the collection of the 48-hour post-dose PK blood draw. Following a 7 day washout interval, all subjects returned to the clinic for Period 2, at which they were administered the Baclofen via the route not administered in Period 1 (oral or IM injection), based on the randomization, and a collection of the same set of blood samples over 48 hours as described above. The PK samples from Periods 1 and 2 were analyzed for plasma baclofen and M1 levels and PK parameters were calculated.

Each subject who completed the study received both baclofen routes of administration (oral and IM injection, 20 mg) doses as randomized, for each treatment period. Authorized site personnel administered each dose of study medication to subjects at the clinic site. All subjects remained at the clinic site for the duration of first 24 hours for each treatment period.

Subjects were fasted from 10 hours before dosing until approximately 4.5 hours after dosing. Following the single dose in each period, subjects were provided a standard diet that was similar in composition during each treatment period. All data was generated using a validated bioanalytical method for Baclofen and its predominant metabolite M1: Baclofen 3-(4-chlorophenyl)-4-hydroxybutyric acid.

Treatment Description

| Treatment | Description |
|---|---|
| Intramuscular | Baclofen IM, 4 mg/mL; 20 mg (5 mL), administered via IM injection.<br>Choice of leg for injection site was noted |
| Oral tablet | Baclofen Oral Tablet, 20 mg; administered orally with 8 ounces of water. |

Food and Fluid Intake

Subjects were fasted for 4 hours prior to the Screening Visit (i.e., refrain from eating or drinking, with the exception of water). Subjects were also refrained from eating or drinking (with the exception of water) for at least 10 hours prior to each administration of study drug. Additionally, with the exception of 8 ounces of water provided at the time of baclofen oral tablet administration, water was prohibited for 1 hour prior to and 1 hour post study drug administration. Lunch was provided approximately 4.5 hours after study drug administration, and dinner was provided approximately 10 hours after the first dose of study drug. Additionally, a light evening snack was allowed approximately 3½ hours after dinner.

Drug Concentration Measurements

Sample Collection and Processing

A dead-volume intravenous catheter was used to subjects for blood collection to avoid multiple skin punctures. Otherwise, blood samples were collected by direct venipuncture.

The total volume of blood drawn from each subject completing this study did not exceed 165 mL.

Blood Samples:

In each period, a total of 16 blood samples were drawn from each subject for determination of baclofen concentrations. All blood samples were drawn into blood collection tubes (1×3 mL) containing di potassium ethylenediaminetetraacetic acid ($K_2$ EDTA). Blood samples were collected prior to drug administration (0.000), 5, 15, 30, 45 minutes, and 1.00, 2.00, 3.00, 4.00, 6.00, 8.00, 10.0, 12.0, 24.0, 36.0, and 48.0 hours post dose in each period. The time tolerance window for blood samples collected during the confinement period was ±1 minute for all samples collected before 8 hours post-dose and ±3 minutes for subsequent samples. The time tolerance window for return visit samples was ±30 minutes.

Sample collections done outside the pre-defined time windows were not considered as protocol deviations since actual post-dose sampling times were used for PK and statistical analyses. Unless otherwise specified or for subject safety, when blood draws and other procedures coincide, blood draws had precedence.

Blood samples were cooled in an ice bath and were centrifuged at 2000±20 g for at least 10 minutes at approximately 4° C. (no more than 240 minutes passed between the time of each blood draw and the start of centrifugation). Two (2) aliquots of at least 0.5 mL (when possible) of plasma were dispensed into polypropylene tubes as soon as possible. The aliquots were transferred to a −20° C. freezer (no more than 180 minutes passed between the start of centrifugation and aliquot storage), pending analysis/shipment to the analytical facility.

At the end of the study, all clinical samples were transferred to the bioanalytical facility (within the same site). The plasma aliquots were received in good condition and still frozen.

Pharmacokinetic Analyses

Handling of the Below the Lower Limit of Quantitation (BLQ) and the No Reportable Concentration Values During PK and statistical analyses, drug concentrations BLQ of an assay was considered as zero except when they occur between two non-BLQ concentrations where they were considered as missing. A sample with a no reportable value occurring prior to the dosing for a given period was replaced by zero. For tabulation, graphical representation and calculation purposes, all samples with no reportable value observed after dosing was set to missing.

Handling of the Difference Between the Scheduled and the Actual Sampling Times

The actual clock time for dosing and the actual clock time for each collection time for the PK samples were recorded using the electronic data capture. For all sampling times, the actual sampling times were calculated as the difference between the sample collection actual clock time and the actual clock time of dosing. The actual post-dose sampling times expressed in hours and rounded off to three decimal digits were used to calculate the PK parameters, except for pre-dose samples occurring prior to dosing, which was always be reported as zero (0.000), regardless of the time difference. In the PK section of the report, scheduled sampling times were presented in concentration tables and mean graphs while actual times were presented for the individual graphs. A listing of the actual times for PKs was provided for PK samples.

Pharmacokinetic Parameters

Plasma samples were used to calculate the following baclofen and M1 PK parameters by standard non-compartmental methods:

| | |
|---|---|
| $AUC_{0-t}$: | Area under the time-concentration curve of plasma baclofen or M1 from time zero until the last quantifiable value. $AUC_{0-t}$ was calculated using the trapezoidal method linear interpolation. |
| $AUC_{0-\infty}$: | Area under the time-concentration curve of plasma baclofen or M1 extrapolated to infinity, calculated as $AUC_{0-t} + C_{last}/\lambda_z$, where $C_{last}$ is the last measurable concentration. |
| Residual Area: | Calculated as $100 * (1 - AUC_{0-t}/AUC_{0-\infty})$. |
| $C_{max}$: | Observed maximum concentration of plasma baclofen or M1. |
| $t_{max}$: | Sampling time of observed maximum plasma concentration of baclofen or M1. |
| $\lambda_z$: | Terminal elimination rate constant of plasma baclofen or M1. |
| $t½$: | Terminal elimination half-life, calculated as $\ln(2)/\lambda_z$. This parameter was the negative of the estimated slope of the linear regression of the log-transformed concentration (natural logarithm) versus time profile in the terminal elimination phase. At least 3 concentration points were used in estimating $\lambda_z$. The time point where log-linear $\lambda_z$ calculation begins ($\lambda_{z\,Lower}$), and the actual sampling time of the last quantifiable concentration used to estimate the $\lambda_z$ ($\lambda_{z\,Upper}$) were reported with the correlation coefficient from the linear regression to calculate $\lambda_z$. |

Statistical Analyses

Individual and mean plasma concentration versus time curves for each treatment were presented using linear and semi-log scales.

Plasma concentrations of each analyte were listed and summarized by study drug treatment for the Per Protocol population using descriptive statistics (number of observations, arithmetic and geometric means, SD, coefficient of variation [CV %], median, Min, and Max).

PK parameters for Baclofen Oral Tablets (20 mg dose) and for Baclofen IM Injection (20 mg dose) were used in the demonstration of BE. The comparison of their systemic absorption and overall PK was based on an 80.00-125.00% C.I. for $C_{max}$, $AUC_{0-t}$, and $AUC_{0-\infty}$. The M1 results were presented as supportive data only.

Plasma PK parameters were listed and summarized by study drug treatment for the Per Protocol population using descriptive statistics. Arithmetic means, SD, Min, Max, median, and CV % were calculated for PK parameters. Geometric mean and CV % were added to the summary statistics for AUCs and $C_{max}$. For the comparison of Baclofen Oral Tablets (20 mg dose) and for Baclofen IM Injection (20 mg dose), additional tables presenting the individual ratios for $C_{max}$, $AUC_{0-t}$, and $AUC_{0-\infty}$, and the individual differences for $t_{max}$ and $t_{1/2}$ were provided.

Whenever a PK parameter was calculated for only one period for a subject, the subject was excluded from the statistical analysis involving this parameter. However, data from the available period was included in the descriptive statistics.

Pharmacokinetic Analysis

The PK parameters calculated for baclofen and baclofen M1 were $AUC_{0-t}$, $AUC_{0-\infty}$, $C_{max}$, $t_{max}$, $\lambda_z$, and $t_{1/2}$. The PK values for the IM and oral tablet treatments (baclofen and M1) are summarized in the tables below.

The following table summarizes parameters for baclofen.

| Pharmacokinetic Parameters of Baclofen | | | | | | |
|---|---|---|---|---|---|---|
| Subjects (No, (M/F) Type | Mean Parameters (+/−SD) | | | | | |
| Age: mean (Range) | $C_{max}$ (ng/mL) | $T_{max}$* (h) | $AUC_{0-t}$ (h*ng/mL) | $AUC_{0-\infty}$ (h*ng/mL) | $T_{1/2}$ (h) | $\lambda_z$ (/h) |
| 31 (10M/21F) | | | Intramuscular Injection | | | |
| Healthy subjects 38.6 (22-55) | 367.76 (+/−110.29) | 0.489 (0.236, 2.988) | 2419.00 (+/−402.03) | 2436.00 (+/−400.57) | 5.15 (+/−0.59) | 0.1363 (+/−0.0147) |
| | | | Oral Tablet | | | |
| | 375.43 (+/−83.66) | 0.986 (0.486, 2.990) | 2133.18 (+/−432.26) | 2150.70 (+/−431.01) | 5.45 (+/−0.66) | 0.1287 (+/−0.0146) |

*Median (Range: minimum and maximum values shown)

The results in the table above are surprising and unexpected. The bioavailability ($AUC_{0-\infty}$) of the IM and oral dosage were not statistically significantly different. While the bioavailability of the oral dosage was roughly calculated to be about 90% of the IM dose, that difference was not significant. This result, again, is in contrast to the results reported by Agarwal et al. and confirm that the dosing of IM baclofen is consistent with that of oral tablets. It is not clear why this result is occurring.

The following table summarizes parameters for M1.

| Pharmacokinetic Parameters of Baclofen | | | | | | |
|---|---|---|---|---|---|---|
| Subjects (No, (M/F) Type | Mean Parameters (+/−SD) | | | | | |
| Age: mean (Range) | $C_{max}$ (ng/mL) | $T_{max}$* (h) | $AUC_{0-t}$ (h*ng/mL) | $AUC_{0-\infty}$ (h*ng/mL) | $T_{1/2}$ (h) | $\lambda_z$ (/h) |
| 31 (10M/21F) | | | Intramuscular Injection | | | |
| Healthy subjects 38.6 (22-55) | 43.62 (+/−13.42) | 5.987 (2.988, 7.961) | 647.69 (+/−248.22) | 670.99 (+/−254.66) | 7.28 (+/−1.47) | 0.0988 (+/−0.0195) |
| | | | Oral Tablet | | | |
| | 54.65 (+/−13.82) | 3.997 (2.007, 7.986) | 664.56 (+/−221.43) | 688.93 (+/−222.70) | 7.56 (+/−1.73) | 0.0971 (+/−0.0268) |

*Median (Range: minimum and maximum values shown)

Ratios for the $C_{max(baclofen)}:C_{max(M1)}$ and $AUC_{(0-t)(bacloren)}:AUC_{(0-t)(M1)}$ can easily be calculated from the information in the tables above. For example, for the IM administration, the $C_{max}$ value for baclofen ($C_{max(bacloren)}$) is 367.76; the $C_{max}$ value for M1 ($C_{max(M1)}$) is 43.62; accordingly, 367.76/43.62 is 8.43, or 8.4 rounded down. Calculated ratios are shown in the table below.

| Treatment | $C_{max(baclofen)}:C_{max(M1)}$ | $AUC_{(0-t)(baclofen)}:AUC_{(0-t)(M1)}$ |
|---|---|---|
| IM | 8.4 | 3.7 |
| Oral tablet | 6.9 | 3.2 |

Here again, the results are surprising. Given that the absolute bioavailability for the IM dosage is not significantly different from the oral dose (apparently not different by more than 10%), we would have expected the ratios for the bioavailability (AUC) and $C_{max}$ for baclofen:M1 to not have differed by more than about 10%. But what we observe is that the ratios do differ by more than 10%, which is surprising.

And again, it is unclear why this is occurring. Regardless of why this is occurring, it provides apparent advantages to the IM formulation relative to the oral formulation. That is, given that 1:1 dosing can be used, the IM would seem to provide advantages by making more of the baclofen available relative to the M1 metabolite, compared to the oral formulation.

The present disclosure includes any combination of these various features or embodiments above and/or below as set forth in sentences and/or paragraphs. Any combination of disclosed features herein is considered part of the present disclosure and no limitation is intended with respect to combinable features.

Applicant specifically incorporates the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the disclosure be limited to the specific values recited when defining a range.

Other embodiments of the present disclosure will be apparent to those skilled in the art from consideration of the present specification and practice of the present disclosure disclosed herein. It is intended that the present specification and examples be considered as exemplary only with a true scope and spirit of the disclosure being indicated by the following claims and equivalents thereof.

The invention claimed is:

1. A method of treating spasticity in a patient comprising: administering by intramuscular administration to the patient an injectable pharmaceutical formulation comprising:
   an effective amount of 4-amino-3-(4-chlorophenyl) butanoic acid (baclofen), and one or more pharmaceutically acceptable excipients;
   wherein the effective amount of baclofen is 20 mg;
   wherein the injectable formulation has a concentration of 4 mg/mL baclofen;
   wherein intramuscularly administering a 20-mg dose of the formulation to the patient produces a $C_{(max)(baclofen)}$ value of from about 257 ng/mL to about 478 ng/mL; and
   the formulation on administration to a patient provides a bioavailability that is not more than 10% different from an oral dose with similar strength.

2. The method according to claim 1, wherein intramuscularly administering a 20-mg dose of the formulation to the patient produces a $C_{(max)(M1)}$ value of from about 30 ng/mL to about 57 ng/mL.

3. The method of claim 1, wherein intramuscularly administering a 20-mg dose of the formulation to the patient produces a ratio $C_{max(baclofen)}:C_{max(M1)}$ of from about 4.5 to about 15.9.

4. The method of claim 3, wherein intramuscularly administering a 20-mg dose of the formulation to the patient produces a ratio $C_{max(baclofen)}:C_{max(M1)}$ of from about 8.0 to about 15.9.

5. The method according to claim 1, wherein intramuscularly administering a 20-mg dose of the formulation to the patient produces a $AUC_{(0-t)(baclofen)}$ value of from about 2017 h·ng/mL to about 2821 h·ng/mL.

6. The method according to claim 1, wherein intramuscularly administering a 20-mg dose of the formulation to the patient produces a $AUC_{(0-t)(M1)}$ value of from about 399 h·ng/mL to about 896 h·ng/mL.

7. The method of claim 1, wherein intramuscularly administering a 20-mg dose of the formulation to the patient produces a ratio $AUC_{(0-t)(baclofen)}:AUC_{(0-t)(M1)}$ of from about 2.3 to about 7.1.

8. The method of claim 7, wherein intramuscularly administering a 20-mg dose of the formulation to the patient produces a ratio $AUC_{(0-t)(baclofen)}:AUC_{(0-t)(M1)}$ of from about 3.5 to about 7.1.

9. The method of claim 8, wherein intramuscularly administering a 20-mg dose of the formulation to the patient produces a ratio $AUC_{(0-t)(baclofen)}:AUC_{(0-t)(M1)}$ of from about 3.6 to about 7.1.

10. The method of claim 1, wherein the spasticity results from multiple sclerosis.

11. The method of claim 1, wherein the spasticity is associated with at least one of flexor spasms, pain, clonus, and muscular rigidity.

12. The method of claim 1, wherein the spasticity results from cerebral palsy, stroke, traumatic brain injury, spinal cord injury, spinal cord disease, or combinations thereof.

* * * * *